US006229006B1

(12) United States Patent
Wu

(10) Patent No.: US 6,229,006 B1
(45) Date of Patent: May 8, 2001

(54) USE OF ANTISENSE OLIGODEOXYNUCLEOTIDES TO PRODUCE TRUNCATED PROTEINS

(75) Inventor: Ding Wen Wu, Devon, PA (US)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 08/770,473

(22) Filed: Dec. 20, 1996

Related U.S. Application Data

(60) Provisional application No. 60/009,097, filed on Dec. 22, 1995.

(51) Int. Cl.[7] .............................. C07H 21/04; C12Q 1/68; A01N 43/04; A61K 31/70
(52) U.S. Cl. ....................... 536/24.5; 536/23.1; 536/24.3; 435/6; 435/91.1; 435/325; 435/375; 514/44
(58) Field of Search ........................... 435/6, 91.1, 91.31, 435/325, 375; 536/23.1, 24.3, 24.5; 514/44

(56) References Cited

FOREIGN PATENT DOCUMENTS

WO 95/13387   5/1995  (WO) .

OTHER PUBLICATIONS

Andrea D. Branch, A good antisense molecule is hard to find, TIBS, 47–48, Feb. 1998.*
Stanley T. Crooke, Basic Principles of Antisense Therapeutics, Springer–Verlag, NY, p. 3, Jul. 1998.*
Jones, S.S.; D'Andrea,A.D.; Haines,L.L.; Wong,G.G.Human erythropoietin receptor: cloning, expression,and biologic characterization.Blood, vol. 76, No. 1, pp. 31–35, 1990.*

R. Wagner, "Gene Inhibition Using Antisense Oligodeoxynucleotides", *Nature*, vol. 372, pp. 333–335 (1994).
Ihle et al., "Cytokine Receptors and Signal Transduction", *Baillier's Clinical Haematology*, vol. 7, pp. 17–48 (1994).
Andrea et al., "The Cytoplasmic Region of the Erythropoietin Receptor Contain Nonoverlapping Positive and Negative Growth–Regulatory Domains", *Molecular and Cellular Biology*, pp. 1980–1987 (1991).
Chapelle et al., "Truncated Erythropoietin Receptor Causes Dominantly Inherited Benign Human Erythrocytosis", *Proc. Natl. Acad. Sci, USA*, vol. 90, pp. 4495–4499 (1993).
Yi et al., Hematopoietic Cell Phosphatase Associates With Erythropoietin (Epo) Receptor After Epo–Induced Receptor Tyrosine Phosphorylation: Identification of Potential Binding Sites, *Blood*, vol. 85, pp. 87–95 (1995).
Jones et al., "Human Erythropoietin Receptor: Cloning, Expression, and Biologic Characterization", *Blood*, vol. 76, pp. 31–35 (1990).
E. Uhlmann and A. Peyman, "Antisense Oligonucleotides: A New Therapeutic Principle", *Chemical Reviews*, vol. 90, pp. 543–584 (1990).
Kitamura et al., Expression Cloning of the Human IL–3 Receptor cDNA Reveals a Shared •Subunit for the Human IL–3 and GM–CSF Receptors, *Cell*, vol. 66, pp. 1165–1174 (1991).

* cited by examiner

Primary Examiner—Robert A. Schwartzman
Assistant Examiner—Janet Epps
(74) Attorney, Agent, or Firm—Kirk Baumeister; William T. King

(57) ABSTRACT

Oligodeoxynucleotides are provided which are targeted to the nucleic acids encoding receptor negative regulatory domains. In a preferred embodiment, the oligodeoxynucleotides are targeted to the EPOR negative regulatory domain. Methods of enhancing cell growth through use of the oligodeoxynucleotides are also provided.

3 Claims, 7 Drawing Sheets

USE OF ANTISENSE OLIGODEOXYNUCLEOTIDES TO PRODUCE TRUNCATED PROTEINS

This application claims benefit under 35 USC 119(e) of U.S. Provisional Application No. 60/009,097, filed Dec. 22, 1995.

FIELD OF THE INVENTION

The present invention relates to antisense oligodeoxynucleotides useful for producing truncated receptor proteins and their uses.

BACKGROUND OF THE INVENTION

An antisense approach is commonly utilized to block the expression of specific genes within cells. See, e.g., R. W. Wagner, Nature 372, 333–335 (1994); and W. Risau, PCT International Publication Number: WO95/13387 (1995). It is hypothesized that RNase H hydrolyses the RNA strand of a RNA-DNA duplex and is likely to be responsible for the antisense effects of 2'-deoxyoligonucleotides. The translation initiation site of a mRNA is often used as the antisense binding site on the assumption that this region is important and accessible. However, recent studies such as those of Risau, supra, indicate that most regions of the mRNA are in fact accessible to oligonucleotides, except for those with strong secondary structure.

It has been shown that the carboxyl terminus (C-terminus) of the erythropoietin receptor (EPOR) is a negative regulation domain for cell growth. See James Ihle et al., Bailliere's Clinical Haemotology 7, 17–48 (1994); and A. D. DeAndrea et al., Mol Cell Biol. 11, 1980–1987 (1991). Further, this view is supported by the following evidence:

(i) In EPOR transfectants of Ba/F3 cells, a 40 amino acid truncation at the C-terminus enhances cell proliferation (DeAndrea et al., supra).

(ii) In a naturally occurring human EPOR mutant, a 70 amino acid truncation at the C-terminus caused erythrocytosis. The affected individuals have excellent or superior health without abnormalities (A. D. L Chapelle et al., Proc. Natl. Acad. Sci. USA 90, 4495–4499 (1993)).

(iii) Hematopoietic cell phosphatase (HCP), which down regulates the EPO-induced cell proliferation, binds to a region close to the C-terminus of EPOR (Taolin Yi et al., Blood 85, 87–95 (1995)).

DETAILED DESCRIPTION OF THE INVENTION

Figure 1:
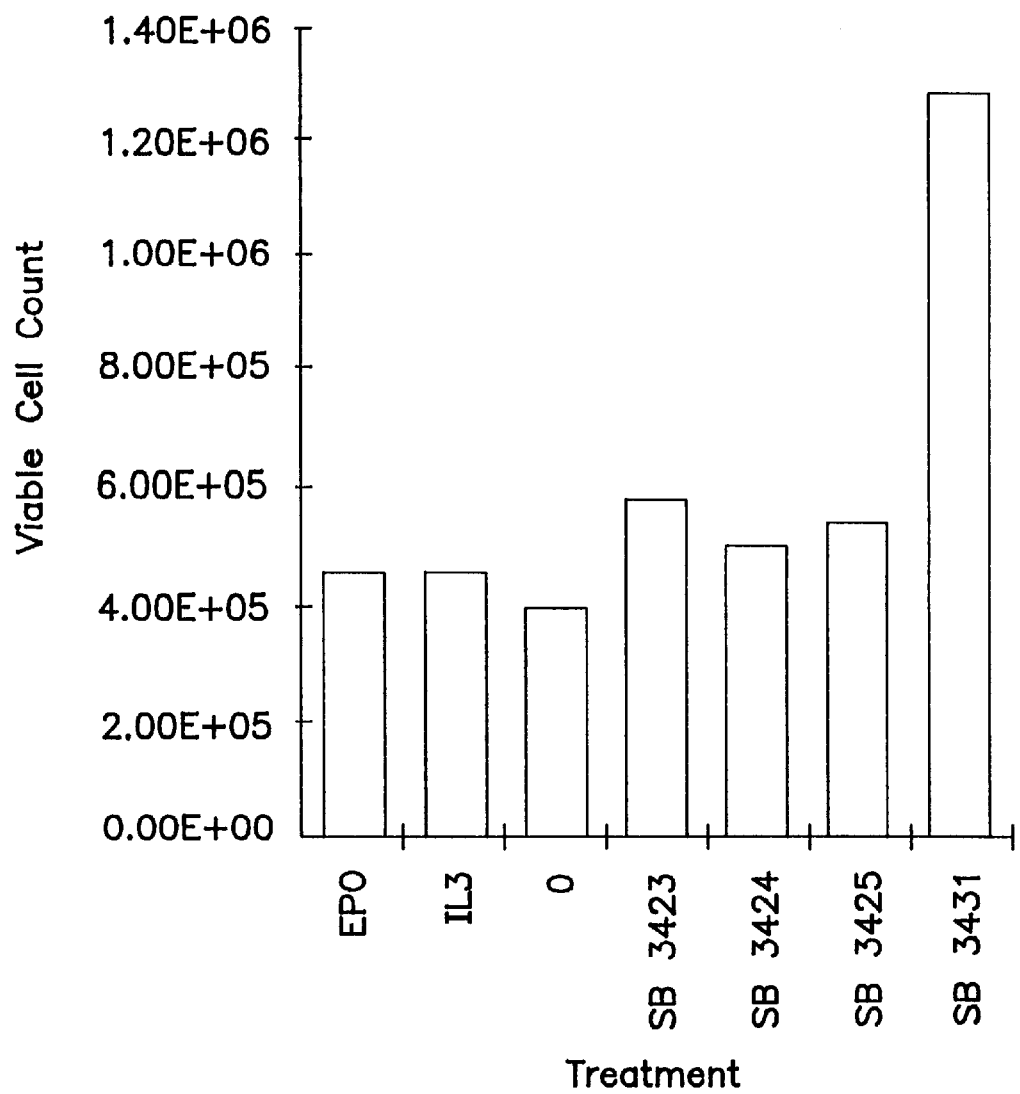
FIG. 1 is a graph of viable cell counts for UT7-EPO cells with various treatments.

The antisense approach of the present invention is not to block EPOR gene expression to shut down erythroid cell growth, but to produce a C-terminally truncated EPOR to enhance cell growth. An antisense phosphorothioate oligodeoxynucleotide, designated SB3431, was rationally designed based on the unique feature of the C-terminus of EPOR. SB3431 was designed to block the 3' translational region of mRNA for production of C-terminally truncated EPOR, in order to truncate the EPOR negative regulatory domain, thereby enhancing erythroid cell growth.

The stabilizing modification of phosphorothioate linkages instead of phosphodiester linkages renders the oligonucleotides of the invention resistant to cellular nuclease digestion and are more preferred. Other preferred linkages resistant to nuclease digestion such as phosphotriester, methyl phosphonate, short chain alkyl or cycloalkyl intersugar linkages or short chain heteroatomic or heterocyclic intersugar linkages could also be used. Other preferred oligonucleotides may contain alkyl and halogen-substituted sugar moieties such as a 2'-O-fluoro, 2'-O-methyl, 2'-O-ethyl or 2'-O-propyl moiety.

SB3431 is complementary to the mRNA region encoding the C-terminus amino acids 478–483 of human EPOR (S. S. Jones et al., Blood 76, 31–35 (1990)) having the sequence SYVACS. The phosphorothioate oligodeoxynucleotide has the sequence:

SB3431: 5'-GAGCAAGCCACATAG-3'    (SEQ ID NO: 1)

Other antisense phosphorothioate oligodeoxynucleotides complementary to a mRNA region encoding a different C-terminus proximal sequence of the human EPOR were designed having the following sequences:

SB3423: 5'-CACAAGGTACAGGTA-3'    (SEQ ID NO: 2)
SB3424: 5'-GTCCCCTGAGCTGTAGTC-3'    (SEQ ID NO: 3)
SB3425: 5'-TCATAAGGGTTGGAGTAG-3'    (SEQ ID NO: 4)

SB3423 is complementary to the mRNA region encoding the C-terminus amino acids 429–433 of human EPOR having the sequence YLYLV. SB3424 is complementary to the mRNA region encoding the C-terminus amino acids 442–447 of human EPOR having the sequence DYSSGD. SB3425 is complementary to the mRNA region encoding the C-terminus amino acids 459–465 of human EPOR having the sequence PYSNPYE.

SB3431 and the other oligodeoxynucleotides of the invention are useful in a method of enhancing erythroid cell growth through their use as agents for specifically enhancing EPO activity for proliferation induction and apoptosis suppression of erythroid precursor cells. In this method of the invention, tissues or cells are contacted with the oligodeoxynucleotide(s). In the context of this invention, to "contact" tissues or cells with an oligodeoxynucleotide or oligodeoxynucleotides means to add the oligodeoxynucleotide(s), usually in a liquid carrier, to a cell suspension or tissue sample, either in vitro or ex vivo, or to administer the oligodeoxynucleotide(s) to cells or tissues within a human.

Further, the compounds of the invention can be used for production of C-terminal truncated EPOR. Also, SB3431 and the other oligodeoxynucleotides of the invention can be used therapeutically for treatment of anemia which is associated with renal diseases, AZT treatment, cancer, myelodysplastic syndromes, rheumatoid arthritis, autologous transfusion, surgery or chemotherapy.

Additionally, SB3431 can be used as a diagnostic tool for negative detection of C-terminal truncated EPOR mutants, such as the naturally occurring mutant in human, by using Northern blotting, PCR, etc., in comparison to the level of C-terminus intact EPOR in the wild type.

A further aspect of the invention is antisense phosphorothioate oligodeoxynucleotide(s) which block a different 3' translational region on mRNA which also produces C-terminally truncated EPOR to enhance erythroid cell growth.

Another aspect of the invention is antisense phosphorothioate oligodeoxynucleotide(s) complementary to the mRNA region encoding the C-terminus sequence of human IL-3 receptor b chain (IL3R b), c-kit or any other receptor having a negative regulatory domain which produces negative regulatory domain truncated receptors to enhance cell growth.

Yet another aspect of the invention is antisense phosphorothioate oligodeoxynucleotide(s) complementary to the mRNA region encoding the HCP binding site of human IL-3 receptor b chain (IL3R b) or c-kit to produce negative regulatory domain truncated receptor to enhance cell growth.

The oligodeoxynucleotides of this invention are also useful for research purposes. The specific hybridization exhibited by the oligodeoxynucleotides may be used for assays, purifications, cellular product preparation and other methodologies which would be appreciated by persons or ordinary skill in the art.

The present invention will now be described with reference to the following specific, non-limiting examples.

EXAMPLE 1

Cell Growth Effects

Studies were conducted on the effect of the designed phosphorothioate oligodeoxynucleotides on cell growth in EPO-dependent UT7-EPO cells (N. Komatsu et al., *Blood* 82, 456–464 (1993)). Cell numbers and viability (trypan blue exclusion) were determined using a hemocytometer. MTT (thiazolyl blue) cell proliferation assays were conducted. First, cell number and viability were determined. If viability was greater than 90%, the cells were washed twice with IMDM cell culture medium containing no added growth factors. The washed cells were suspended in the medium at a cell density of $8 \times 10^5$ or $1 \times 10^6$ cells/mL. The cells were then split into 96-well plates at 100 uL/well for different treatments. The antisense oligodeoxynucleotides were added to 5 uM. Growth factor controls contained 1 U/mL EPO (Amgen) or 10 ng/mL IL3 (R&D Systems). Cells with no treatment were used as the control. The cells were incubated at 37° C. in 5–7.5% $CO_2$ for 24, 48 or 72 hours. Four hours before the end of the incubation, 25 uL of MTT (Sigma, Product No. M 2128 made to 1.6 mg/mL in PBS and sterile filtered) were added per well. The plates were then incubated at 37° C. in 5–7.5% $CO_2$ for 4 hr. 100 uL of 10% SDS/0.01N HCl were added to each well four hours after the MTT addition. The plates were placed in an incubator until the formazan crystals dissolved (3–4 h if plates shaken while incubated or overnight). OD readings of each plate well were determined in an ELISA plate reader having a 570 nm test filter and a 750 nm reference filter.

Figure 2A:
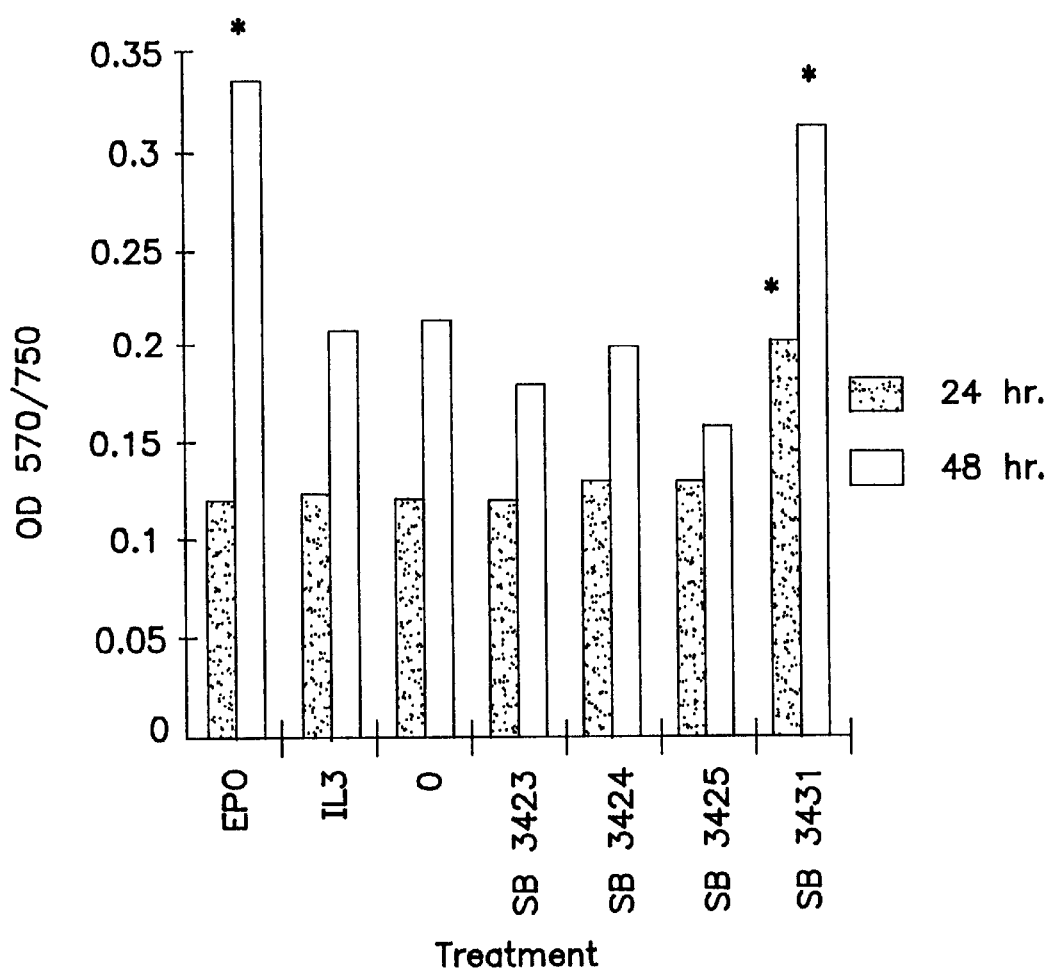
FIG. 2 is a graph of MTT assay results for UT7-EPO cells with various treatments.
Figure 2B:
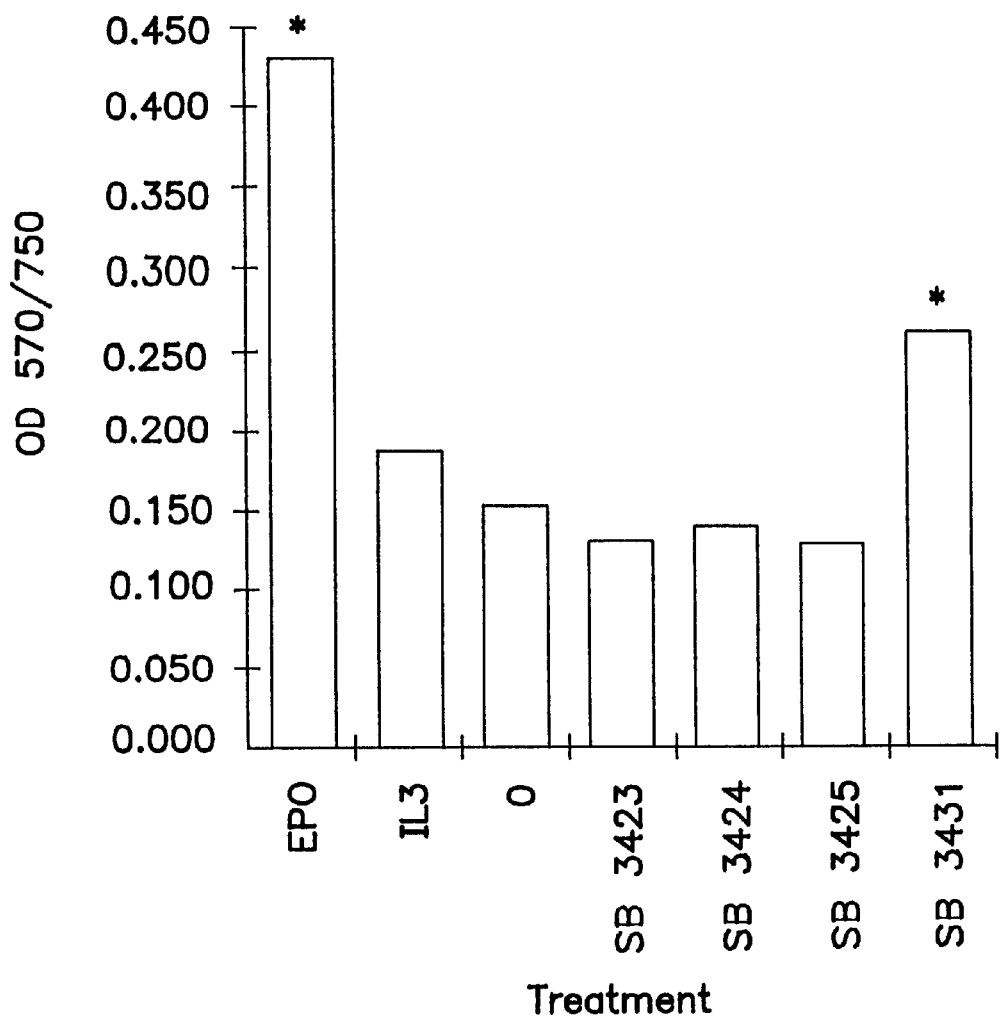

The experimental results presented in FIGS. 1 and 2 and Table 1 demonstrate that SB3431 is active for stimulation of cell growth in EPO-dependent human UT7-EPO cells. SB3431 promoted cell growth at concentrations of 5 uM, while similar concentrations of SB3423, SB3424 and SB3425 did not significantly increase cell growth.

Figure 3A:
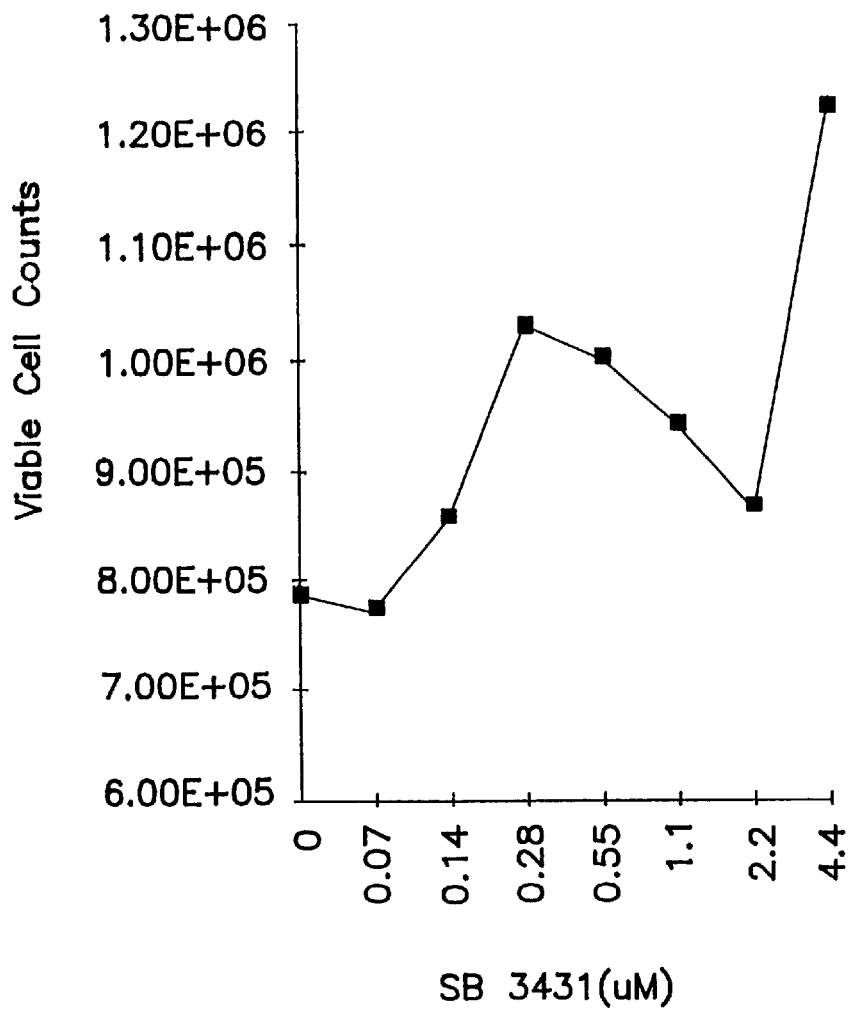
FIG. 3 is a graph of the effect of SB3431 on viable cell counts and viability in UT7-EPO cells.
Figure 3B:
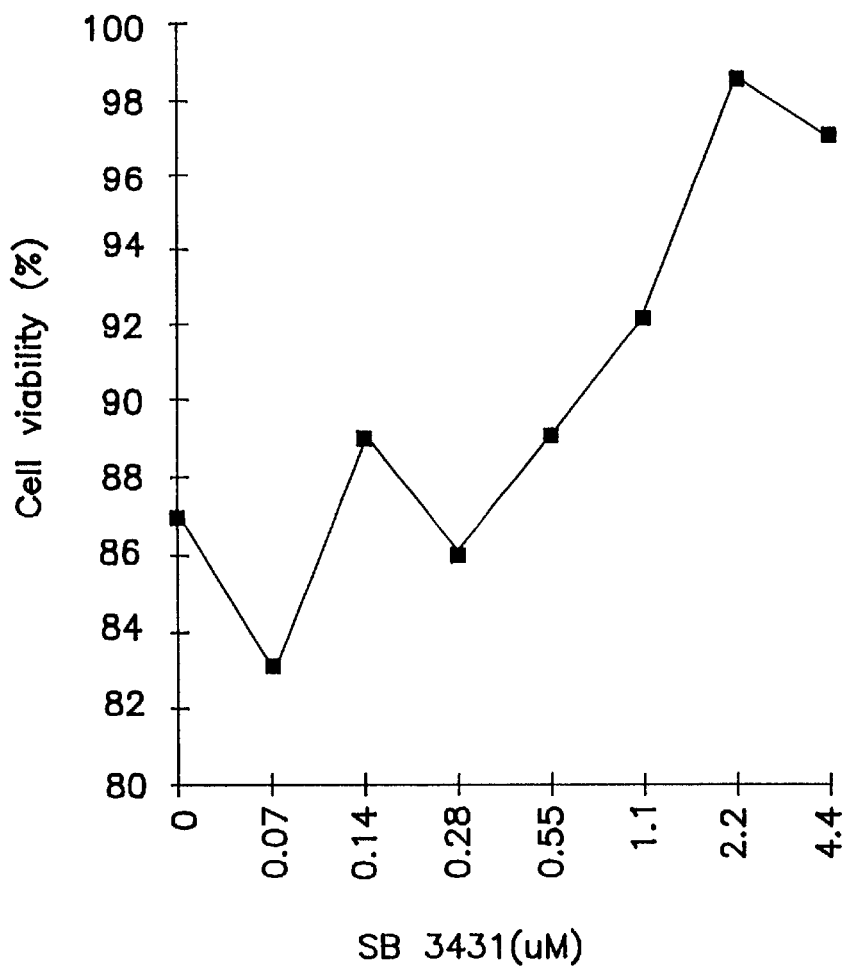

Dose response curves were generated in the presence of from 0.07 uM to 4.4 uM SB3431 as described above. The experimental results presented in FIG. 3 demonstrate that SB3431 promotes cell growth in UT7-EPO cells in a dose-dependent fashion.

EXAMPLE 2

Effect on Apoptosis

The effect of the designed phosphorothioate oligodeoxynucleotides on apoptosis in EPO-dependent UT7-EPO cells was also studied. Cells with a viability of greater than 90% were washed extensively with IMDM medium without fetal bovine serum and EPO. The cells were then incubated in the medium at 37° C. for 24–48 hrs. The EPO depletion in the medium induces apoptosis in the cells, which is used as a positive control for DNA ladder formation. Cells were treated with 1 U/mL EPO (Amgen) as a negative control for apoptosis. To test the anti-apoptotic activity of the antisense deoxyoligonucleotides, the EPO-starved cells were treated with the compounds for the same time period.

DNA ladder formation was determined by pelleting about $1 \times 10^7$ cells at 600×g for 5 minutes at 2° C. in 15 mL conical bottom tubes. The supernatant was discarded and the cell pellets kept on ice. The cells were lysed in a digestion buffer of 10 mM Tris Cl, pH 7.5, 5 mM EDTA, pH 8 and 0.2% SDS in a portion of $6 \times 10^6$ cells/75 uL buffer. RNase-It cocktail (Strategene) was added to a final concentration of 50 U/100 uL. The mixture was incubated for 15–20 minutes at 37° C. with agitation. Proteinase K (1 mg/mL in 10 mM $CaCl_2$) was added at a concentration of 200 ug/mL and the mixture incubated 15–20 minutes at 65° C. with agitation. The lysates were kept on ice. Samples for electrophoresis on 2% agarose gels were prepared by adding a 1/4 volume of a loading buffer containing 50% glycerol, 0.05 M EDTA, 0.25% bromophenol blue and 1% SDS and incubating at 65° C. for 5 minutes prior to loading and electrophoresis.

The 360 bp, 540 bp and/or 720 bp bands of the apoptotic DNA ladder were selected and quantified on a densitometer (BioImage). The experimental results presented in Table 2 demonstrate that SB3431 suppresses apoptosis in EPO-dependent human UT7-EPO cells. SB3431 reduced apoptosis at concentrations of 5 uM, while similar concentrations of SB3423, SB3424 and SB3425 did not significantly decrease apoptosis.

Figure 4:
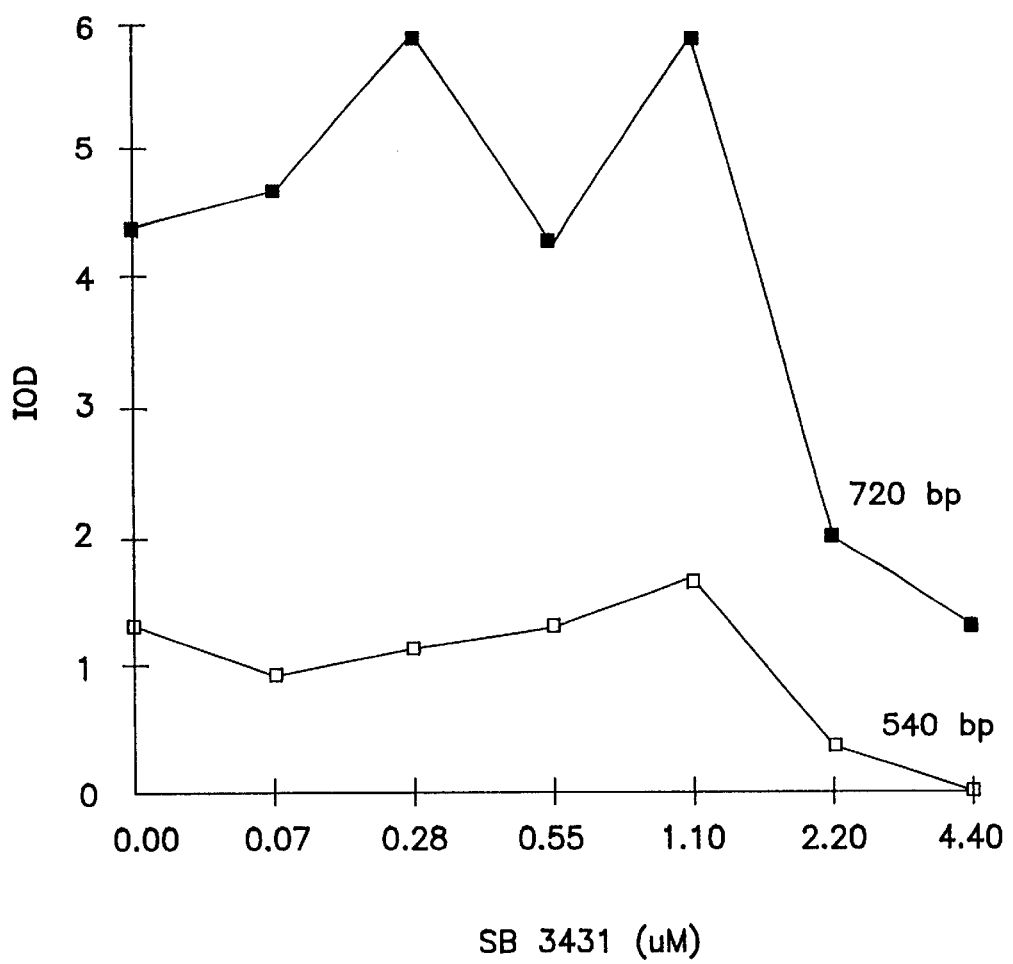
FIG. 4 is a graph of DNA ladder assay results for dose response of SB3431 in UT7-EPO cells.

Dose response curves were generated in the presence of from 0.07 uM to 4.4 uM SB3431 as described above. The experimental results of the quick DNA ladder assay for SB3431 dose response in EPO-dependent human UT7-EPO cells presented in FIG. 4 demonstrated that SB3431 reduces apoptosis in UT7-EPO cells in a dose-dependent fashion.

EXAMPLE 3

Effect on EPO Response

Figure 5:
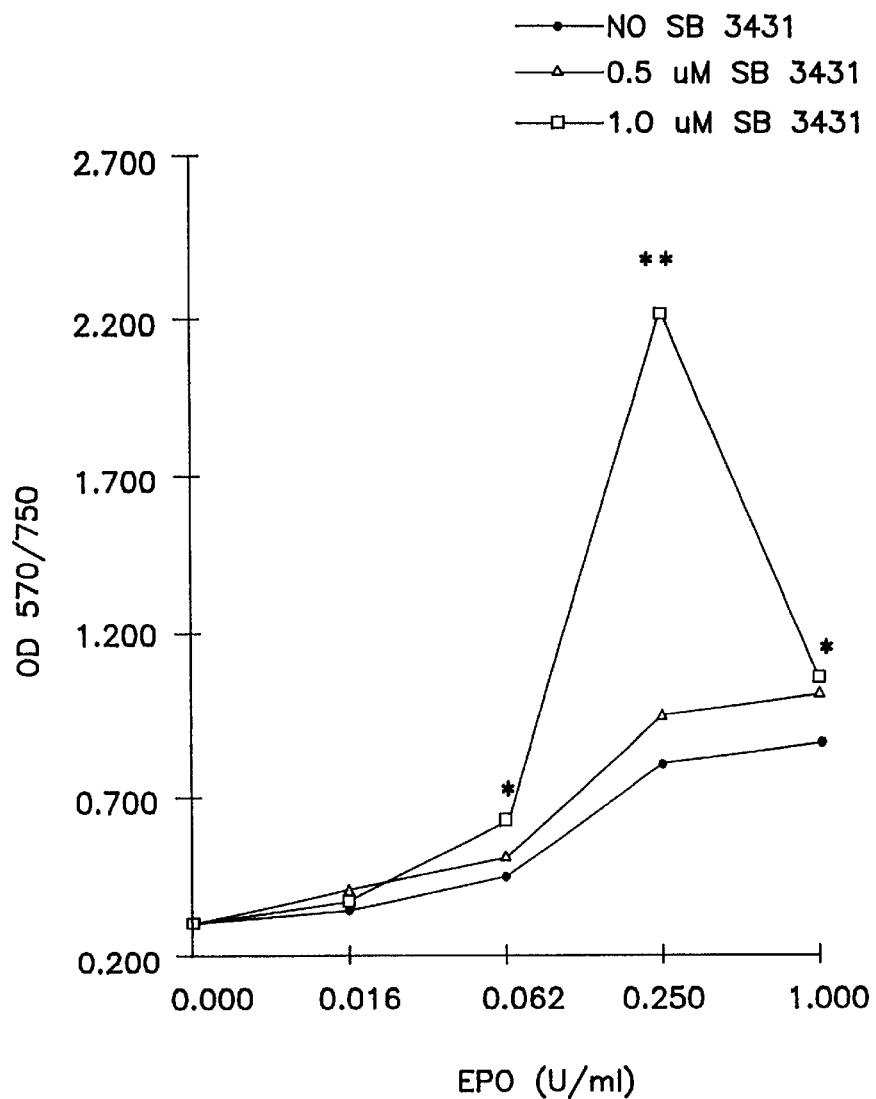
FIG. 5 is a graph of MTT assay results for SB3431 effect on EPO response of UT7-EPO cells.

The effect of the designed phosphorothioate oligodeoxynucleotides on EPO response in EPO-dependent UT7-EPO cells was also studied. MTT cell proliferation and DNA ladder assays were performed as described above. The experimental results presented in FIG. 5 (MTT assay) and the DNA ladder assay (data not shown) demonstrated that SB3431 enhances EPO response in UT7-EPO cells.

Further experiments indicated that SB3431 does not induce cell growth in non-EPO-responsive HL-60 cells (data not shown). Further, it was demonstrated that EPOR mRNA is not degraded by RNAse H after SB3431 treatment of the cells (data not shown). While not intending to be bound by any particular theory, it is possible that SB3431 causes the truncation of a negative regulatory region of EPOR.

SB3431 is specific to EPOR, i.e., it specifically enhances EPO-induced cell growth and apoptosis suppression. Further, it does not block HCP or other negative regulatory protein binding to other receptors.

The present invention may be embodied in other specific forms without departing from the spirit or essential attributes thereof, and, accordingly, reference should be made to the appended claims, rather than to the foregoing specification, as indicating the scope of the invention.

What is claimed is:

1. An oligodeoxynucleotide consisting of the nucleotide sequence as set forth in SEQ ID NO:1.

2. The oligodeoxynucleotide of claim 1 comprising at least one phosphorothioate internucleoside linkage.

3. A method of enhancing erythroid cell growth comprising contacting tissue or cells in vitro with an oligodeoxynucleotide consisting of the nucleotide sequence as set forth in SEQ ID NO:1.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO: 1:

GAGCAAGCCA CATAG                                                           15

(2) INFORMATION FOR SEQ ID NO: 2:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (xi) SEQUENCE DESCRIPTION: SEQ ID NO: 2:

CACAAGGTAC AGGTA                                                           15

(2) INFORMATION FOR SEQ ID NO: 3:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO: 3:

GTCCCCTGAG CTGTAGTC                                                        18

(2) INFORMATION FOR SEQ ID NO: 4:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO: 4:

TCATAAGGGT TGGAGTAG                                                        18